United States Patent [19]

Cooper

[11] Patent Number: 5,621,144

[45] Date of Patent: Apr. 15, 1997

[54] FLUORINATED COMPOUNDS AS OXYGEN TRANSPORT AGENTS

[75] Inventor: Stephen R. Cooper, Maryland Heights, Mo.

[73] Assignee: Isis Innovation Limited, Oxford, Great Britain

[21] Appl. No.: 370,239

[22] Filed: Jan. 9, 1995

Related U.S. Application Data

[63] Continuation of Ser. No. 90,187, filed as PCT/GB92/02208, Nov. 23, 1992, published as WO93/11098, Jun. 10, 1993, abandoned.

[30] Foreign Application Priority Data

Nov. 29, 1991 [GB] United Kingdom ............... 9125454

[51] Int. Cl.$^6$ .................................. C07C 233/12
[52] U.S. Cl. ............... 564/189; 560/172; 560/184; 564/14; 564/84; 564/95; 564/209; 564/297; 564/510; 568/669; 568/684; 568/842
[58] Field of Search ........................... 564/189, 209, 564/14, 84, 95, 297, 510; 514/617, 625, 628; 560/172, 184; 568/669, 684, 842

[56] References Cited

U.S. PATENT DOCUMENTS

| | | | |
|---|---|---|---|
| 3,133,965 | 5/1964 | Amann et al. | 564/209 |
| 3,655,677 | 4/1972 | Anello et al. | 564/189 |
| 4,985,550 | 1/1991 | Charpiot et al. | 536/18.4 |

FOREIGN PATENT DOCUMENTS

| | | | |
|---|---|---|---|
| 1618090 | 11/1970 | Germany . | |
| 2154574 | 5/1972 | Germany . | |
| 2731226 | 1/1979 | Germany . | |
| 1938744 | 2/1979 | Germany . | |
| 0265398 | 3/1989 | Germany | 564/209 |
| 55-035020 | 3/1980 | Japan | 564/209 |
| 55-147218 | 11/1980 | Japan | 514/628 |
| 1269730 | 4/1972 | United Kingdom . | |
| 1338430 | 11/1973 | United Kingdom . | |

*Primary Examiner*—Shailendra Kumar
*Attorney, Agent, or Firm*—Wenderoth, Lind & Ponack

[57] ABSTRACT

New compounds are described typically having the formula $CH_3C(CH_2R)_3$ or $ZCH_2C(CH_2R)_3$ where R is a fluorohydrocarbon or perfluorocarbon group, preferably containing 4–16 carbon atoms and more F atoms that H atoms. Z is a hydrophilic group which may make the compound self-emulsifiable. The compounds are useful as oxygen transport agents in vivo, for which purpose aqueous emulsions are used, as a blood substitute.

8 Claims, No Drawings

FLUORINATED COMPOUNDS AS OXYGEN TRANSPORT AGENTS

This application is a continuation of application Ser. No. 08/090,187, filed as PCT/GB92/02208 Nov. 23, 1992 published as WO93/11098, Jun. 10, 1993, now abandoned.

This invention concerns new highly fluorinated compounds (perfluorocarbons) for use as oxygen transport agents in vivo. Potential and realised applications of perfluorocarbon (PFC) emulsions primarily involve their use as blood substitutes. Specific applications include their use in treatment or management of myocardial[1] and cerebral[2] ischaemia and aplastic anemias, as radiosensitisers for radiation therapy, in organ preservation, as blood substitutes for veterinary use and for those with religious objections to human blood, for drug delivery, and as $^{19}$F MRI contrast agents.

For physiological use perfluorocarbons must be administered as emulsions to avoid inducing liquid/liquid emboli. Present PFC emulsions result from mixtures of PFCs with surfactants. For example, Fluosol-DA (Green Cross Corp., Japan) consists of a mixture of perfluorodecalin with perfluorotri-n-butylamine emulsified with egg yolk phospholipids and Pluronic F-68 (a polydisperse block copolymer of ethylene and propylene oxides). The reticuloendothelial system strips Fluosol-DA of its surfactants and deposits the PFCs in adipose tissue[3]. Blood lipoproteins eventually deliver perfluorodecalin to the lung, where it is exhaled, but perfluorotributylamine remains essentially forever in the liver. Management of PFC excretion therefore forms a critical aspect of blood substitute technology.

U.S. Pat. No. 4,985,550 describes compounds having a polyhydroxylated hydrophilic moiety, a highly fluorinated moiety and a functional junction group linking said moieties together. These compounds are used as surfactants in emulsions containing also perfluorocarbons as oxygen transport agents. Surfactants compounds containing one or at most two highly fluorinated moieties per molecule are disclosed.

As oxygen transport agents in vivo, known perfluorocarbon compounds suffer from two disadvantages. The first is the difficulty of getting enough oxygen transport capacity into emulsion form. This arises because the solubility of oxygen in the perfluorocarbon is not very high (though much higher than in water), and because it is difficult or impossible to form emulsions containing high concentrations of the perfluorocarbons. The second problem is that mentioned above regarding excretion. The present invention addresses these problems, and in its preferred forms should overcome both of them.

In one aspect, the invention provides a compound for use in vivo as an oxygen transport agent, said compound comprising at least one linking group carrying at least three highly fluorinated arms. The compound may have the structure $LR_n$, where R is a highly fluorinated arm, n is 3 or 4, and L is a linking group.

Perfluorocarbons dissolve large quantities of oxygen because they interact only weakly with each other, and therefore leave cavities into which oxygen molecules can intercalate. Previous studies have emphasised the role of molecular shape in determining oxygen solubility in perfluorocarbons and other liquids. Such compounds may have several conformations, in which the highly fluorinated arms may or may not be adjacent or associated with one another. In preferred compounds, a predominant conformation is one in which the arms co-operate to form an oxygen-binding pocket. High oxygen solubility is associated with the presence of vacant cavities in the liquid, and consequently higher oxygen affinities should result from the use of highly fluorinated arms to provide oxygen-binding pockets. In other fields, pre-formed pockets are known to dramatically increase the solubility of desired species such as alkali or alkaline earth metal ions. In the clinical context, more efficient oxygen transport agents will allow administration of smaller quantities of perfluorocarbon for the same therapeutic effect.

Preferred compounds according to the invention also include a substantially non-hemolytic hydrophilic group. This hydrophilic group tends to make the compound emulsifiable in water or saline, in the preferred case even self-emulsifiable without the need for any co-surfactant. Examples of preferred compounds according to the invention are the following

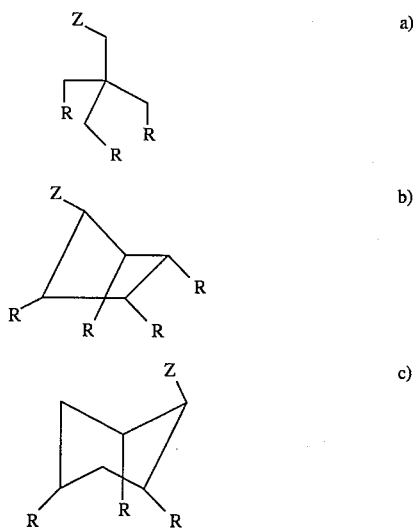

In these structures, Z is the hydrophilic group and R is a highly fluorinated arm. The lines represent carbon chains, with each angle or junction representing a carbon atom to which are attached the appropriate number of hydrogen atoms. Preferred linking groups are substantially non-fluorinated, i.e. few or none of the C—H bonds have been replaced by C—F bonds. Preferred linking groups are three-dimensional carbon frameworks including alicyclic ring structures, bearing at least three sites for attachment of highly fluorinated arms and preferably another site for attachment of a surfactant group. Such groups may be derived from linking moieties such as propane, isobutane, neo-pentane, cyclopentane or cyclohexane. Specific examples are tris(1,1,1-trihydroxymethyl)ethylamine, pentaerythritol, 5-substituted-1,2,3,4-cis, cis, cis-cyclopentane tetracarboxylic acid, and 6-substituted-1,3,5-cis, cis-triaminocyclohexane.

The preferred feature that the compound have an oxygen-binding pocket implies that the three or more highly fluorinated arms be associated in some defined way. Thus, tri(p-erfluoroalkyl)amines do not have oxygen-binding pockets in the sense of this invention; nor do the trans isomers of the preferred linking moieties mentioned above.

The three or more highly fluorinated arms of the compound may be the same or different but are usually the same. Preferably each arm has more C—F bonds than C—H bonds. Preferably the end of each arm (remote from the linking group) is perfluorinated, i.e. contains only C—F bonds to the exclusion of C—H bonds. Preferably each highly fluorinated arm is a C4 to C16 hydrocarbon, saturated or unsaturated, straight chained or branched or cyclic, aromatic or heterocyclic, in which more than half the H atoms are replaced by F atoms. Examples of such arms include the following:

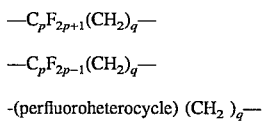

-(perfluoroheterocycle) $(CH_2)_q-$ where p is 4 to 12, and q is 0 to 4 and the heterocycle is a 5 or 6 membered ring containing 1 or 2 oxygen or nitrogen atoms. Preferably the preformed highly fluorinated arms are joined to a linking group by any conventional covalent bond, for example an ether, ester, amide, amine, sulphonamide or phosphoramide bond. Highly fluorinated alkanoyl halides, sulphonyl halides and alkyl ethylenes are all commercially available. These compounds can be conjugated by standard chemical techniques to tripodal or tetrapodal amines (also known and commercially available) to give chemically robust amides or amines.

Preferred compounds according to the invention include also a substantially non-hemolytic hydrophilic group. The function of this group is to make the compound emulsifiable in water or saline, preferably in the absence of any extraneous surface active agent. However, a co-surfactant may nevertheless be required, and for this purpose those described for example in U.S. Pat. No. 4,985,550 (mentioned above ) are suitable. The nature of the hydrophilic group is not material to the invention. A lot of work has been done on non-hemolytic surfactants[4]. Examples of suitable surfactant groups include the following:

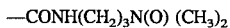

and

Preferably the hydrophilic group is joined to the linking group, by conventional chemical methods, prior to attachment of the highly fluorinated arms.

The above description has focused mainly on compounds in which three or four highly fluorinated groups and one hydrophilic are attached to a linking group. As will be apparent, compounds with two or more hydrophilic groups are possible. Also compounds containing two or more linking groups, joined through surfactant groups or through highly fluorinated arms, are possible and are included within the scope of the invention.

The compounds are emulsifiable in water or saline, by the use of a conventional surfactant which may be a perfluorsurfactant. Preferred compounds, as noted above, are emulsifiable without the need for added surfactant. The resulting aqueous emulsions, preferably containing 5–70% by volume of the compound, are suitable for administration, generally by injection into the blood stream of the patient. When the compounds are being used as oxygen carriers in place of red blood cells, up to 0.5 to 1 liters may be required in the human blood stream. For use at these high concentrations, the compounds need to be substantially non-toxic. They should not be significantly metabolised in vivo. They should be non-hemolytic, and this is readily achieved by suitable choice of hydrophilic groups in accordance with known criteria. They should be non-immunogenic. And they should preferably be excretable by a renal excretion pathway. Incorporation of the highly fluorinated arms with a hydrophilic group makes excretion subject to control; choice of available hydrophilic groups enables manipulation of the dwell time from 1 day to months or more (for use in management of e.g. aplastic anemias). Structurally the compounds resemble the metabolic products of non-polar xenobiotics which commonly undergo hepatic oxidation (by microsomal cytochrome P-450) and conjugation to highly polar groups (e.g. glucuronic acid or glycine) to permit their urinary excretion.

Synthesis of Head-Substituted 1,1,1-tri-(aminomethyl) ethane

Preparation of head-substituted 1,1,1-tri-(aminomethyl)-ethane proceeds from alkylation of sodio diethyl malonate, followed by treatment with formaldehyde and base in $Me_2SO$ and reduction ($NaBH_4$/LiCl/diglyme) to give the cyano-substituted triol (see below). Tosylation followed by treatment with sodium diformylamide gives the cyano-substituted triamine; acid-catalysed hydrolysis of the nitrile and esterification with MeOH yields the required methyl ester of the triamine trihydrochloride. This route has already been optimised in the inventors laboratory.

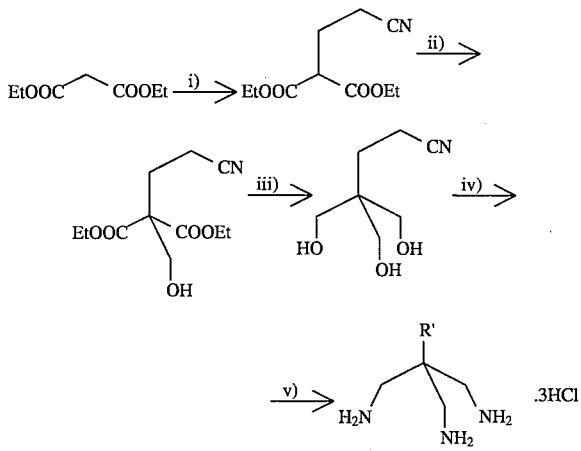

i) NaOEt/EtOH, $CH_2CHCN$;

ii) NCHO/$Me_2SO$/⁻OH;

iii) $NaBH_4$/LiCl/diglyme;

iv) TsCl/DMAP/pyr; $Na^+$ $^{-N(CHO)}{}_2$ R=$CH_2CH_2CN$;

v) $H^+$, NeOH

Synthesis of PFC pockets

Carboxamide and sulphonamide-based ligands are prepared by reaction of the appropriate acid chloride with the triamine hydrochloride with $Et_3N$ used as base to deprotonate the triamine and to neutralise protons released during reaction. For example, ($R_f$ designates a highly fluorinated arm):

(1)

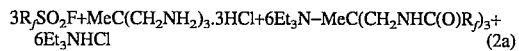

(2a)

Carboxamide-based ligands are synthesised from the appropriate commercially-available esters ($C_7F_{15}$COOEt, $C_8F_{17}$COOMe, $C_9F_{19}$COOEt) as exemplified by the reaction

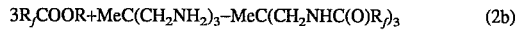

(2b)

which is carried out in the corresponding alcohol, ROH.

Alkyl-linked ligands are prepared by direct addition of the amine group to perfluoro-substituted ethylene, $R_f$CHF=$CH_2$, according to

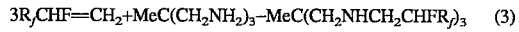

(3)

REFERENCES 1. a) Reduction of Myocardial-Ischemia During Percutaneous Transluminal Coronary Angioplasty with Oxygenated Fluosol; Kent, K. M.; Cleman M. W.; Cowley, M. J.; Forman, M. B.; Jaffe, C. C.; Kaplan, M.; King, S. B.; Krucoff, M. W.; Lassar, T.; McAuley, B.; Smith, R.; Wisdom, C.; Am. J. Cardiol., 1990, 66, 279–284.

b) Blood-Free Reperfusion with Fluosol-DA Reduces Myocardial Infarct Size and Improves Left-Ventricular Function; Schaer, G. L.; Santoian, E. C.; Visner, M. S.; Virmani, R.; Gold, C. L.; Karas, S. P.; Clin. Res., 1988, 36, A314–A314.

c) Reduction in reperfusion injury by blood-free reperfusion after experimental myocardial infarction. Schaer, G. L.; Karas, S. P.; Santoian, E. C.; Visner, M. S.; Virmani, R.; J. Am. Coll. Cardiol, 1990, 15, 1385–93.

2. a) Local Cerebral Glucose-Metabolism After Global-Ischemia— Treatment by Ventriculocisternal Perfusion with a Fluorocarbon Emulsion; Triolo, A. J.; Osterholm, J. Lo; Alexander, G. M.; Bell, R. D.; Fraser, G. D.; Neurosurg., 1990, 26, 480–488.

b) Effects of fluosol-DA on brain edema, energy metabolites, and tissue oxygen content in acute cerebral ischemia; Memesawa, H.; Katayama, Y.; Shimizu, J.; Suzuki, S.; Kashiwagi, F.; Kamiya, T.; Terashi, A.; Adv. Neurol., 1990, 52, 109–18.

3. The safety and efficacy of perfluorochemical emulsions as blood substitutes. Sloviter,. H. A.; Biomater. Artif. Cells Artif. Organs, 1988, 16 459–61.

4. Riess, J. G.; S. Pace and L. Zarif; (1991). "Highly Effective Surfactants with Low Hemolytic Activity." Advan. Mater. 3 (5): 249–251.

In the following Experimental Section, a typical procedure is followed by the characteristics of one or more compounds prepared by the general procedure described.

EXPERIMENTAL SECTION

I General procedures

Proton ($^1$H), carbon ($^{13}$C), and fluorine ($^{19}$F) NMR are recorded with a Bruker AM 300 spectrometer operating at 300 MHz and the chemical shifts are reported in parts per million (ppm) relative to tetramethylsilane (TMS) for all $^1$H and $^{13}$C NMR. spectra.

The IR, spectra are determined as thin films, mujol mulls or KBr disks with Mattson Polaris FTIR, or Perkin-Elmer 1710 FTIR spectrometer. Melting points are determined with Gallenkamp apparatus and the values obtained are not corrected.

The surface tension measurements are made with Dognon Abribat tensiometer by the Wilhelmy method.

Thin layer chromatography is carried out on silica gel plates.

All anhydrous solvents are purchased from Aldrich Chemical Company and are used without further purification.

II Activation of alcohols a) Tosylates i) Typical procedure. Dissolve 42 g (350 mmol; 1 eq.) tris(hydroxymethyl)ethane in 100 mL pyridine and place it in a 500 mL three-neck round bottomed flask equipped with a thermometer, magnetic stirrer bar and addition funnel. Cool the solution to 0° C. and add to it a solution of 240 g (1260 mmol; 3.6 eq) tosyl chloride in 200 mL pyridine dropwise. After addition, allow the mixture to warm to room temperature and stir for additional 12 hr. Pour it into a mixture of 200 mL water, 500 mL methanol and 200 mL concentrated hydrochloric acid (the resulting supernatant must be slightly acidic, if not, then add more of the acid). Filter the white precipitate, wash it thoroughly with water, and a little methanol. Dry the solid under vacuum and recrystallise it from methanol/ethyl acetate.

ii) Characteristics

Tris(tosyloxymethyl)ethane [$CH_3C(CH_2OSO_2C_6H_4$-p-$CH_3)_3$], white solid, recrystallise from methanol/ethyl acetate, yield 70%, m.pt. 106° C., IR(KBr) 3050, 1595, 1150 cm$^{-1}$; $^1$H NMR (CDCl$_3$) δ7.7 and 7.4 (d, 12H, C$_6$H$_4$), 3.75 (s, 6H, CH$_2$O), 2.50 (s, 9H, pCH$_3$), 0.9 (s, 3H, CH$_3$C).

Tris(tosyloxypropyl)nitromethane [$O_2NC(CH_2CH_2CH_2OSO_2C_6H_4$-p-$CH_3)_3$], purify by dry flash chromatography (SiO$_2$, 50%, EtOAc in hexane), yellow gum, yield 80%, R$_f$=0.74(EtOAc), IR(film) 3093, 3067, 2970, 2900, 1598, 1537 cm$^{-1}$; $^1$;H NMR (CDCl$_3$) δ7.8 and 7.4 (d, J =8.2 Hz, 12H, C$_6$H$_4$), 4.00 (t, J=5.7 Hz, 6H, CH$_2$O), 2.50 (s, 9H, pCH$_3$), 1.9 (m, 6H, CH$_2$), 1.5 (m, 6H, CH$_2$).

Trioryethylenemethyltosyl ether [$CH_3O(CH_2CH_2O)_3SO_2C_6H_4$-p-$CH_3$], purify by dry flash chromatography (SiO$_2$, 20%, EtOAc in Hexane), pale yellow liquid, yield 86%, R$_f$=0.68(EtOAc), IR(film) 3095, 2800, 1600, 1150, 1100 cm$^{-1}$; $^1$H NMR (CDCl$_3$) δ7.7 and 7.4 (d, J=8.2 Hz, 4H, C$_6$H$_4$), 3.7 (m, 12H, OCH$_2$CH$_2$O), 3.38 (s, 3H, CH$_3$O) 2.4 (s, 3H, pCH$_3$).

b) Mesylates i) Typical procedure. Place 411 mL dichloromethane and 137 g (1196 mmol; 3.5 eq.) mesyl chloride in a round bottomed flask and cool the mixture to −5° C. Add very slowly a mixture of 94.6 g (1196 mmol; 3.5 eq.) pyridine and 41 g (341 mmol; 1 eq.) tris(hydroxymethyl)ethane to the flask— this takes about 90 min. After reaction, allow the mixture to warm up to room temperature and stir for additional 4 hr. Filter the white solid by suction and wash it with 30 mL dichloromethane. Combine the flitrate, dry over MgSO$_4$ and remove the solvent on rotary evaporator to leave a pale yellow viscous liquid which crystallises as white needles on standing.

ii) Characteristics

Tris(mesyloxymethyl)ethane [$CH_3C(CH_2OSO_2CH_3)_3$], white solid recrystallise from EtOAc/hexane, yield 82%, $^1$H NMR (CDCl$_3$) δ4.18 (s, 6H, CH$_2$O), 3.08 (s, 9H, CH$_3$SO$_2$), 1.17 (s, 3H, CH$_3$C).

Trs(mesyloxypropyl)nitromethane [$O_2NC(CH_2CH_2CH_2OSO_2CH_3)_3$], purify by dry flash chromatography (SiO$_2$, 5% methanol in EtOAc), pale yellow viscous oil, yield 85%, R$_f$=0.46 (EtOAc), IR(film) 3031, 2942, 1538, 1456, 1353 cm$^{-1}$, $^1$H NMR (CDCl$_3$) δ4.39 (t, J=5.90 Hz , 6H, CH$_2$O), 3.05 (s, 9H, CH$_3$SO$_2$), 2.1 (m, 6H, CH$_2$C) 1.7 (m, 6H, CH$_2$C).

Dioxyethylenemesylmethyl ether [$CH_3O(CH_2CH_2O)_2SO_2CH_3$] purify by dry flash chromatography (SiO$_2$, 50%, EtOAc in hexane), colourless liquid, yield 93%, R$_f$=0.52 (EtOAc), $^1$H NMR (CDCl$_3$) δ4.34 (m, 2H, CH$_2$OSO$_2$), 3.48–3.72 (m, 6H, CH$_2$CH$_2$O), 3.31 (s, 3H, CH$_3$O), 3.02 (s, 3H, CH$_3$SO$_2$).

Trioxyethylenemesylmethyl ether [$CH_3O(CH_2CH_2O)_3SO_2CH_3$] purify by dry flash chromatography (SiO$_2$, 50% EtOAc in hexane), colourless liquid, yield 88%, R$_f$= 0.48 (EtOAc), $^1$H NMR (CDCl$_3$) δ4.34 (m, 2H, CH$_2$OSO$_2$), 3.48–3.72 (m, 10H, CH$_2$CH$_2$O), 3.31 (s, 3H, CH$_3$O), 3.02 (s, 3H, CH$_3$SO$_2$).

Tetraoxyethylenemesylmethyl ether [CH$_3$O(CH$_2$CH$_2$O)$_4$SO$_2$CH$_3$], purify by dry flash chromatography (SiO$_2$, 50% EtOAc in hexane), colourless liquid, yield 75%, R$_f$=0.42 (EtOAc), $^1$H NMR (CDCl$_3$) δ4.34 (m, 2H, CH$_2$OSO$_2$), 3.48–3.72 (m, 14H, CH$_2$CH$_2$O), 3.31 (s, 3H, CH$_3$O), 3.02 (s, 3H, CH$_3$SO$_2$).

Dioxyethylenebenzylmesyl ether [C$_6$H$_5$CH$_2$O(CH$_2$CH$_2$O)$_2$SO$_2$CH$_3$], pale red liquid, yield 93%, R$_f$=0.58 (EtOAc), IR, (film) 3030, 1604, 1104 cm$^{-1}$, $^1$H NMR, (CDCl$_3$) δ7.3 (m, 5H, C$_6$H$_5$), 4.55(s, 2H, CH$_2$Bz), 4.35 (m, 2H, CH$_2$OSO$_2$), 3.65 (m, 6H, CH$_2$O), 3.0 (s, 3H, CH$_3$SO$_2$).

1H,1H-perfluoroheptylmesyl ether [C$_6$F$_{13}$CH$_2$OSO$_2$CH$_3$], purify by dry flash chromatography (SiO$_2$, 30%, EtOAc in hexane), colourless liquid, yield 75%, IR (film) 033, 2048, 1126 cm$^{-1}$, $^1$H NMR (CDCl$_3$) δ4.65 (t, 2H, CH$_2$O), 3.1 (s, 3H, CH$_3$SO$_2$).

c) Triflates i) Typical procedure. Place 15 mL dichloromethane and 5.0 g (17.7 mmol; 3.2 eq.) trifluoromethanesulphonic anhydride in a 50 mL round bottomed flask. Cool the solution to −5° C. and add a mixture of 1.4 g (17.7 mmol; 3.2 eq.) pyridine and 0.7 g (5.5 mmol; 1 eq.) tris(hydroxymethyl)ethane dropwise to the flask— this takes about 5 min. Allow the mixture to warm to room temperature and stir for another 5 min. Filter it through a short column (70–230 mesh SiO$_2$) and wash the white precipitate with 10 mL dichloromethane. Evaporate the solvent on a rotary evaporator to yield a colourless liquid.

ii) Characteristics

Tris(trifyloxymethyl)ethane [CH$_3$C(CH$_2$OSO$_2$CF$_3$)$_3$], colourless viscous oil, yield 71%, R$_f$=0.45 (EtOAc), IR (film) 2986, 1142 cm$^{-1}$, $^1$H NMR (CDCl$_3$) δ4.48 (s, 2H, CH$_2$O), 1.28 (s, 3H, CH$_3$C).

Tris(trifyloxymethyl)nitromethane, [O$_2$NC(CH$_2$OSO$_2$CF$_3$)$_3$], colourless liquid, yield 73%, $^1$H NMR (CDCl$_3$) δ5.0 (s, 2H, CH$_2$O).

III Ether linkages a.i) Typical Procedure I. Carefully weigh 1.3 g sodium hydride (60% dispersion in mineral oil) and transfer it to an oven dried 50 mL three-neck round bottomed flask equipped with a thermometer, an addition funnel, a nitrogen inlet and a magnetic stirrer bar. Flush the flask with dry nitrogen and close it with a septum. Add 5 mL dried and freshly distilled hexane. Swirl the flask, allow the sodium hydride to settle, and then carefully remove the supernatant liquid by syringe. Repeat this washing procedure twice, and then add 20 mL anhydrous tetrahydrofuran (THF) to the flask by syringe. Start the stirrer and add by addition funnel a suspension of 1.2 g (10.2 mmol; 1 eq.) tris(hydroxymethyl)ethane in 10 mL THF at room temperature over a period of 20 min. Stir the mixture for additional 10 min and add 5.0 g (32.8 mmol; 3.2 eq.) butyloxy mesylate in 5 mL anhydrous THF to the solution dropwise at room temperature. After addition, replace the addition funnel by a water reflux condenser and reflux the mixture for 16 hr. Cool the mixture to room temperature and carefully pour the reaction mixture into a beaker containing 20 mL water. Transfer the dilute mixture to a separatory funnel and extract the product with 3×15 mL portions of diethyl ether. Combine the organic extracts and dry them over MgSO$_4$. Filter off the drying agent by suction and remove the filtrate on rotary evaporator. Wash the product through dry flash chromatography column (SiO$_2$) with 50% EtOAc in hexane. A colourless liquid is obtained.
Note * All apparatus must be thoroughly dried in a hot oven (>120° C.) before use. This is because sodium hydride reacts violently with moisture to liberate hydrogen with the risk of fire. * This method is not suitable for the preparation of tripodal-fluoroalkyl compounds because it involves the formation of a carbocation intermediate—a mechanism not favoured by the electron-withdrawing fluoroalkyl group.

a.ii) Characteristics

Tris(butyloxymethyl)ethane [CH$_3$C(CH$_2$OCH$_2$CH$_2$CH$_3$)$_3$], purify by dry flash chromatography (SiO$_2$, 20% EtOAc in hexane), colourless liquid, yield 76%, R$_f$=0.73 (EtOAc), $^1$H NMR (CDCl$_3$) δ3.4 (t, 6H, OCH$_2$), 3.15 (s, 6H, CH$_2$O), 1.5 (m, 6H, CH$_2$C).

Tris(benzyloxydiethyleneoxymethyl)ethane [CH$_3$C(CH$_2$(OCH$_2$CH$_2$)$_2$OCH$_2$C$_6$H$_5$)$_3$], purify by dry flash chromatography (SiO$_2$, 20% EtOAc in hexane), pale yellow oil, yield 57%, R$_f$=0.50 (EtOAc), IR(film) 3030 cm$^{-1}$, $^1$H NMR (CDCl$_3$) δ7.35 (m, 15H, C$_6$H$_5$) 4.6 (s, 6H, CH$_2$Ph), 3.6 (m, 24H, CH$_2$CH$_2$O), 3.3 (s, 6H, CH$_2$O), 0.95 (s, 6H, CH$_3$C).

b.i) Typical Procedure IL Place a solution of 7.8 g (22.4 mmol; 3 eq.) 1H,1H-perfluoroheptan-1-ol in 10 mL anhydrous p-dioxane in a 100 mL round bottomed flask equipped with a stirrer bar, thermometer, nitrogen inlet and condenser. Rapidly weigh out 4.2 g (74.5 mmol; 10 eq.) solid potassium hydroxide and transfer it to an oven dried mortar. Grind the pellets into fine powder and add it to the reaction flask while stirring the alcohol solution vigorously at room temperature under nitrogen (the KOH powder must be well dispersed in the medium). Stir the mixture for 10 min. Dissolve 3.5 g (7.5 mmol; 1 eq.) tris(mesyloxypropyl)nitromethane in 20 mL dry p-dioxane and add 2 mL anhydrous dimethylformamide (DMF) to the solution. Transfer the resulting clear solution to the reaction flask and reflux the mixture for 36 hr. After reaction is complete, cool the mixture to room temperature and pour it to a beaker containing 30 mL water. Transfer the dilute mixture to a separatory funnel and extract the product with 3×15 mL dichloromethane. Dry the combined organic extracts over MgSO$_4$ and remove the solvent on rotary evaporator. Purification by dry flash chromatography with hexane: ethyl acetate (70:30) yields a pale yellow liquid.
Note * Potassium hydroxide is very hygroscopic.

b.ii) Characteristics

Tris(1H,1H-perfluorobutyloxypropyl)nitromethane [O$_2$NC(CH$_2$CH$_2$CH$_2$OCH$_2$C$_3$F$_7$)$_3$], purify by dry flash chromatography (SiO$_2$, 40% EtOAc in hexane) pale yellow oil, yield. 52%, $^1$H NMR (CDCl$_3$) δ3.91 (t, J=13.6 Hz, 6H, CH$_2$CF$_2$), 3.6 (t, J=5.8 Hz, 6H, CH$_2$O), 2.04 (m, 6H, CH$_2$C), 1.55 (m, 6H, CH$_2$C).

Tris(1H,1H-perfluoroheptyloxypropyl)nitromethane [O$_2$NC(CH$_2$CH$_2$CH$_2$OCH$_2$C$_6$F$_{13}$)$_3$], purify by dry flash chromatography (SiO$_2$, 40% EtOAc in hexane) pale yellow oil, yield 50%, $^1$H NMR, (CDCl$_3$) δ3.91 (t, J=13.6 Hz, 6H, CH$_2$CF$_2$), 3.6 (t, J=5.8 Hz, 6H, CH$_2$O), 2.04 (m, 6H, CH$_2$C), 1.55 (m, 6H, CH$_2$C).

[Bis(trifyloxymethyl)-1H,1H-perfluorobutyloxymethyl] ethane [CH$_3$C(CH$_2$OSO$_2$CF$_3$)$_2$CH$_2$OCH$_2$C$_3$F$_7$], yield 40%, $^1$H NMR (CDCl$_3$) δ4.49 (d, J=5.9 Hz, 2H, CH$_2$OSO$_2$), 4.4.37 (d, J=5.9 Hz, 2H, CH$_2$OSO$_2$), 4.0 (t, J=12.1 Hz, 2H, CH$_2$CF$_2$), 3.7 (s, 2H, CH$_2$O), 1.33 (s, 3H, CH$_3$C).

IV Ester linkages i) Typical Procedure. Set up a 50 mL round bottomed flask with an addition funnel, magnetic stirrer bar and nitrogen inlet. Flush the flask with nitrogen and add 20 mL anhydrous THF, 4.5 g (44.1 mmol; 4.5 eq.) triethylamine and 1.2 g (9.8 mmol; 1 eq.) tris(hydroxymethyl)ethane to the flask. Add a few drops of pyridine, with stirring, until a clear solution is obtained, and then cool the solution to −5° C. in an ice/ acetone bath. Place 10 mL anhydrous THF and 8.0 g (34.3 mmol; 3.5 eq.) perfluorobutanoyl chloride in the addition funnel and add the solution to the flask at such a rate as to maintain the reaction temperature below 5° C. After addition is complete, allow the mixture to warm up to room temperature and stir for additional 4 hr. Transfer the mixture to a separatory funnel and add 30 mL diethyl ether. Wash the ethereal solution with 3×15 mL water and dry the organic layer over sodium sulphate. Filter off the drying agent by suction and evaporate the filtrate on a rotary evaporator to leave a colourless liquid.

Note * Acid halides are easily hyrdolysed to the corresponding carboxylic acids. * Reaction of I equivalent of the triol and 3 equivalents of the acid chloride in pyridine at 0° C. gives the disubstituted ester.

ii) Characteristics

Ethanetris(methylperfluorobutanoate) [$CH_3C(CH_2OC(O)C_3F_7)_3$], purify by dry flash chromatography ($SiO_2$, 50% $Et_2O$ in hexane), colourless liquid, yield 90%, $R_f$=0.52 ($Et_2O$/hexane, 1:1), IR (film) 3466, 1790, 1147 $cm^{-1}$, $^1H$ NMR ($CDCl_3$) δ4.35 (s, 6H, $CH_2O$), 1.2 (s, 3H, $CH_3C$).

Ethanetris(methylperfluorooctanoate) [$CH_3C(CH_2OC(O)C_7F_{15})_3$], purify by dry flash chromatography ($SiO_2$, 50%, $Et_2O$ in hexane), colourless liquid, yield 90%, $R_f$=0.52 ($Et_2O$/hexane, 1:1), IR (film) 3466, 1790, 1147 $cm^{-1}$, $^1H$ NMR ($CDCl_3$) δ4.35 (s, 6H, $CH_2O$), 1.2 (s, 3H, $CH_3C$).

Ethanetris(methylethanoate) [$CH_3C(CH_2OC(O)CH_3)_3$], pure colourless liquid, yield 83%, $R_f$=0.55 (EtOAc), IR (film) 3466, 1741, $cm^{-1}$, $^1H$ NMR ($CDCl_3$) δ3.74 (s, 6H, $CH_2O$), 1.8 g (s, 9H, $CH_3CO$), 0.78 (s, 3H, $CH_3C$).

Ethanetris(methylhexanoate) [$CH_3C(CH_2OC(O)CH_2CH_2CH_2CH_3)_3$], pure colourless viscous liquid, yield 88%, very soluble in most organic solvents, IR (film) 1741 $cm^{-1}$, $^1H$ NMR ($CDCl_3$) δ3.98 (s, 6H, $CH_2O$), 2.26 (t, 6H, $CH_2CO$), 1.58 (q, 6H, $CH_2C$), 1.26 (m, 12H, $CH_2CH_2C$), 0.98 (s, 3H, $CH_3C$), 0.83 (t, 9H, $CH_3C$).

Nitromethanetris(methylhexanoate) [$O_2NC(CH_2OC(O)CH_2CH_2CH_2CH_2CH_3)_3$], purify by dry flash chromatography ($SiO_2$, 5% EtOAc in hexane), colourless liquid, yield 87%, $R_f$=0.63 (EtOAc), IR (film) 1752, 1560 $cm^{-1}$, $^1H$ NMR ($CDCl_3$) δ4.48 (s, 6H, $CH_2O$), 2.28 (t, J=7.4 Hz, 6H, $CH_2CO$), 1.57 (q, J=7.4 Hz, 6H, $CH_2C$), 1.25 (m, 12H, $CH_2CH_2C$), 0.84 (t, J=6.8 Hz, 9H, $CH_3C$).

V Amide linkages a) Azides i) Typical Procedure. Equip a 100 mL three neck round bottomed flask with a magnetic stirrer bar, thermometer and water reflux condenser. Add 10 mL anhydrous DMF, 20g (308 mmol; 5 eq.) sodium azide and 21.8 g (62 mmol; 1 eq.) tris(mesyloxymethyl)ethane. Gradually heat the mixture to 100° C. and leave it at this temperature for 12 hr. After the reaction is complete, cool the mixture to room temperature. Filter the white solid formed by suction and wash it with 2×20 mL diethyl ether. Combine the filtrates and wash them with water (3×15 mL) until the organic layer becomes colourless. Dry this layer over $MgSO_4$ and evaporate the solvent under reduced pressure to leave a colourless liquid.

Note * Azides cart cause explosion hazards. * Preparefluoroalkyl azides from the corresponding iodides.

ii) Characteristics

Tris(azidomethyl)ethane [$CH_3C(CH_2N_3)_3$], pure colourless liquid, yield 80%, IR (film) 2099 $cm^{-1}$, $^1H$ NMR ($CDCl_3$) δ3.27 (s, 6H, $CH_2N$), 0.98 (s, 3H, $CH_3C$).

1-azido-1H,1H,2H,2H-perfluorooctane [$C_6F_{13}CH_2CH_2N_3$], pale orange liquid, yield 78%, $R_f$=0.72 (EtOAc), IR (film) 2109, 1146, $cm^{-1}$, $^1H$ NMR ($CDCl_3$) δ3.62 (t, J=7.25 Hz, 2H, $CH_2CF_2$), 2.4 (m, 2H, $CH_2N$).

b) Amines i) Typical procedure. Place an oven dried 250 mL round bottomed flask in a glove box, and place a stirrer bar and 60 mL anhydrous THF in the flask. Weigh out 4.1 g (107.5 mmol; 4.2 eq.) lithium aluminium hydride in the box and carefully add it to the flask. Cork the flask necks with septum stoppers and quickly transfer it to a fume cupboard. Replace the septum with nitrogen inlet, thermometer and addition funnel. Place 10 mL anhydrous THF and 5 g (25.6 mmol; 1 eq.) tris(azidomethyl)ethane in the addition funnel and add the solution to the reaction flask dropwise (90 min). After the addition is complete, replace the addition funnel with a water reflux condenser and reflux the mixture for 18 hr. Cool the mixture to room temperature and carefully add 5 mL water, 5 mL aqueous sodium hydroxide w/w) and more 15 mL water in that order. Transfer the white slurry formed to an extraction thimble and place it in soxhlet apparatus. Extract the product with THF for 24 hr, and then evaporate the solvent on a rotary evaporator and add 10 mL benzene to the oil residue. Reflux the mixture azeotropically with a Dean-Stark trap for 3 hr and evaporate the benzene to leave a very viscous colourless liquid.

Note * All apparatus must be thoroughly dried ii) Characteristics

Tris(aminomethyl)ethane [$CH_3C(CH_2NH_2)_3$], pure colourless gum, yield 70%, IR (film) 3369, 3293, 1603 $cm^{-1}$, $^1H$ NMR ($CDCl_3$) δ2.54 (s, 6H, $CH_2N$), 1.07 (s, 6H, $NH_2$) 0.76 (s, 3H, $CH_3C$).

1H,1H,2H,2H-perfluorooctylamine [$C_6F_{13}CH_2CH_2NH_2$], pure colourless liquid, yield 62%, IR (film) 3500, 3300, 1600, 1140 $cm^{-1}$, $^1H$ NMR ($CDCl_3$) δ3.1 (t, 2H, $CH_2N$), 2.25 (m, 2H, $CH_2CF_2$), 1.5 (s, 2H, $NH_2$).

c) Amides a.i) Typical procedure L Add 5 mL anhydrous THF, 3.3 g (32.9 mmol; 4.5 eq.) triethylamine and 0.86 g (7.3 mmol; 1 eq.) tris(aminomethyl)ethane to a 50 mL round bottomed flask. Cool the mixture to −5° C. and add a solution of 5.3 g (22.6 mmol; 3.1 eq.) perfluorobutanoyl chloride in 10 mL anhydrous THF dropwise to it under nitrogen. Allow the mixture to warm up to room temperature and stir for additional 7 hr. After reaction is complete, pour the mixture into 10 mL cold water. Two layers are formed. Collect the lower layer and extract the upper one with 2×10 mL diethyl ether. Combine the collected lower layer with the ethereal fractions and dry them over $MgSO_4$. Evaporate the solvent on a rotary evaporator to yield a pale yellow viscous oil. Add 10 mL chloroform to the oil, filter the white powder formed by suction and dry the solid under vacuum.

a.ii) Characteristics

Ethanetris(N-methylperfluorobutyramide) [$CH_3C(CH_2NHC(O)C_3F_7)_3$], white solid, recrystallise from chloroform, yield 75%, $^1H$ NMR (DMSO-$d_6$) δ9.34 (s, 3H, NH), 3.17 (s, 6H, $CH_2N$), 0.77 (s, 3H, $CH_3C$).

Ethanetris(N-methylhexyramide) [$CH_3C(CH_2NHC(O)CH_2CH_2CH_2CH_2CH_3)_3$], purify by dry flash chromatography ($SiO_2$, EtOAc), colourless viscous liquid, yield 72%, IR (film) 3303, 1657, 1544, 1463 $cm^{-1}$, $^1H$ NMR ($CDCl_3$) δ7.2 (s, 3H, NH), 2.9 (d, 6H, $CH_2N$), 2.2 (t, 6H, $CH_2CO$), 1.6 (q, 6H, $CH_2C$), 1.25 (m, 12H, $CH_2CH_2$), 0.9 (t, 9H, $CH_3C$), 0.78 (s, 3H, $CH_3C$).

b.i) Typical procedure II. Place 3 g (10.8 mmol) nitromethanetrispropanoic acid and 15 mL thionyl chloride in a 50 mL round bottomed flask equipped with a water reflux condenser, drying tube filled with soda lime and magnetic stirrer bar. Reflux gently over paraffin oil bath for 12 hr. At the end of reaction, transfer the mixture to a single-neck round bottomed flask and carefully remove the excess thionyl chloride on a rotary evaporator at room temperature to leave a pale red viscous oil. Dissolve this oil in 10 mL anhydrous THF, transfer it back into the 3-neck reaction flask and cool the mixture to 0° C. Place a mixture of 3.6 g (35.6 mmol; 3.3 eq.) hexylamine and 3.8 g (37.8 mmol; 3.5 eq.) triethyl amine in an addition funnel, and add it dropwise to the acid chloride solution. Treat the mixture as in Procedure I above.

b.ii) Characteristics

Nitromethanetris(N-hexylpropyramide) [$O_2NC(CH_2CH_2C(O)NHCH_2CH_2CH_2CH_2CH_2CH_3)_3$], purify by dry flash chromatography ($SiO_2$, 30% EtOAc in hexane), pale red oil, yield 55%, $R_f$=0.6 (EtOAc), $^1H$ NMR (CDCl$_3$) δ5.8 (s, 3H, NH), 3.2 (q, 6H, CH$_2$N), 2.25 (t, 6H, CH$_2$CNO$_2$), 2.15 (t, 6H, CH$_2$CO), 1.5 (q, 6H, CH$_2$C), 1.3 (m, 18H, CH$_2$CH$_2$CH$_2$), 0.9 (s, 9H, CH$_3$C).

VI Incorporation of methylene spacer unit

At least one methylene separator is required to functionalise of the quaternary carbon in-order to couple the hydrophilic head group to it.

Typical procedure. Add dropwise 1.2 g (20.3 mmol; 4.5 eq.) anhydrous nitromethane to a suspension of 0.63 g (60% dispersion in mineral oil) sodium hydride in 25 mL dimethyl sulphoxide (DMSO). Stir the mixture for 10 min and add 2 g (4.5 mmol; 1 eq.) tris(hexanoylmethyl)nitromethane in 6 mL DMSO dropwise to the reaction mixture. After addition is complete, the mixture gives a yellow solution. Heat the solution to 65° C. and irradiate it with a 300 W incandescent lamp. At this stage the solution changes from yellow to deep red. Remove the source of heat and irradiation after 20 min, allow the solution to cool to room temperature and salt for additional 3 hr. Add 2 mL acetic acid to the mixture and pour it into a 500 mL flask containing 200 mL water. Extract the product with 4×50 mL ethyl acetate and wash the organic phase with brine. Dry it over MgSO$_4$, filter, and remove the solvent on a rotary evaporator. Elute the pale yellow product with 10% ethyl acetate in hexane using dry flash chromatography column (SiO$_2$).

ii) Characteristics

2-Nitroethane-1,1,1-tris(methylhexanoate) [$O_2NCH_2C(CH_2OC(O)C_5H_{11})_3$], purify by dry flash chromatography (SiO$_2$, 10% EtOAc in hexane), pale yellow liquid, yield 57%, $R_f$=0.80 (EtOAc), IR (film) 1746, 1558 cm$^{-1}$, $^1H$ NMR (CDCl$_3$) δ4.54 (s, 2H, CH$_2$NO$_2$), 4.17 (s, 6H, CH$_2$O), 2.28 (t, 6H, CH$_2$CO), 1.59 (q, 6H, CH$_2$C), 1.26 (m, 12H, CH$_2$CH$_2$C), 0.87 (t, J=6.7, 9H, CH$_3$C).

VII Incorporation of methylacrylate

[CH$_3$OC(O)CH$_2$CH$_2$C(CH$_2$CH$_2$CH$_2$OCH$_2$C$_3$F$_7$)$_3$],

Place a mixture of 1 g (1.3 mmol; 1 eq.) tris(1H,1H-perfluorobutyloxypropyl)nitromethane, 1.3 g (15.4 mmol; 12 eq.)methyl acrylate, 1.1 g (3.8 mmol; 3 eq.) tributyltin hydride, 0.2 g (1.3 mmol; 1 eq.) azobisisobutyronitrile and 1 mL benzene in a 50 mL round bottomed flask. Heat the mixture to 100° C. and stir at this temperature for 20 min. Cool the mixture to room temperature and purify it by dry flash chromatography (SiO$_2$; hexane/benzene) to yield a pale yellow liquid.
Note * Use similar method to prepare the acrylonitrile homologue.

VIII Hydrophilic head group a) Tritylation of diethanolamine i) Typical procedure. Place 27 mL anhydrous DMF and 6.7 g (63.7 mmol; 2.2 eq.) diethanolamine in a 100 mL round bottomed flask equipped with a thermometer, addition funnel and magnetic stirrer bat. Cool the solution to 0° C. and add a solution of 8.0 g (28.7 mmol; 1 eq.) trityl chloride dropwise. Stir the mixture at this temperature for 12 hr, allow it to warm to room temperature and stir for additional 12 hr. Pour the mixture into 20 mL diethyl ether contained in a 100 mL conical flask and add 30 mL water. Place the flask in an ice bath to form a white precipitate. Filter and dry the solid under vacuum. Recrystallise the product from chloroform/hexane.

ii) Characteristics

Trityl-N,N-diethanolamine [(C$_6$H$_5$)$_3$CN(CH$_2$CH$_2$OH)$_2$], white solid, recrstallise from CHCl$_3$/hexane, yield 62%, M.pt. 150° C., $R_f$=0.5 (50% EtOAc/hexane), IR (KBr) 3600, 3100 cm$^{-1}$, $^1H$ NMR(CDCl$_3$) δ7.4 (m, 15H, C$_6$H$_5$), 3.8 (t, 4H, CH$_2$O), 2.6 (t, 4H, CH$_2$N), 2.2 (s, 2H, OH).

b) Homologation with oxyethylenemonomethyl ether i) Typical procedure. Place a mixture of 19.0 g (54.8 mmol; 1 eq.) trityl-N,N-diethanolamine and 75 mL anhydrous THF in a 3-neck round bottomed flask equipped with a nitrogen inlet, water reflux condenser and thermometer. Grind 37 g (660 mmol; 12 eq.) KOH pellets and quickly add the powder into the amine solution while stirring the mixture vigorously in order to disperse the KOH in the reaction medium. After 10 min, add 24 g (121 mmol; 2.2 eq.) dioxyethylene mesylmethyl ether to the reaction mixture and reflux for 16 hr. After reaction, allow the mixture to cool to room temperature, and then pour it into 400 mL water. Rinse the flask with 2×100 mL portions of water and combine the aqueous portions. Extract the product with 4×200 mL diethyl ether. Combine the ether fractions, dry over Na$_2$SO$_4$, and remove the solvent on rotary evaporator to leave a pale yellow liquid. Purify the product by dry flash chromatography (SiO$_2$; 20% ethyl acetate in hexane).

Trityl-N,N-bis(monomethyldioxyethylene)amine [(C$_6$H$_5$)$_3$CN((CH$_2$CH$_2$O)$_2$CH$_3$)$_2$], purify by dry flash chromatography (SiO$_2$, 20% EtOAc in hexane), yield 85%. $R_f$=0.42 (EtOAc), $^1H$ NMR (CDCl$_3$) δ7.1–7.8 (m, 15H, C$_6$H$_5$), 3.32–3.71 (m, 12H, CH$_2$CH$_2$O), 3.3 (s, 6H, CH$_3$O), 2.5 (t, 4H, CH$_2$N).

Trityl-N,N-bis(monomethyltrioxyethylene)amine [(C$_6$H$_5$)$_3$N[(CH$_2$CH$_2$O)$_3$CH$_3$]$_2$], purify by dry flash chromatography (SiO$_2$, 20% EtOAc in hexane), yield 80%, $R_f$=0.35 (EtOAc), $^1H$ NMR (CDCl$_3$) δ7.1–7.8 (m, 15H, C$_6$H$_5$), 3.32–3.71 (m, 20H, CH$_2$CH$_2$O), 3.3 (s, 6H, CH$_3$O), 2.5 (t, 4H, CH$_2$N).

Trityl-N,N-bis(monomethyltetraoxyethylene)amine [(C$_6$H$_5$)$_3$N[(CH$_2$CH$_2$O)$_4$CH$_3$]$_2$], purity by dry flash chromatography (SiO$_2$, 20% EtOAc in hexane), yield 73%, $^1H$ NMR (CDCl$_3$) δ7.1–7.8 g (m, 15H, C$_6$H$_5$), 3.32–3.71 (m, 28H, CH$_2$CH$_2$O), 3.3 (s, 6H, CH$_3$O), 2.5 (t, 4H, CH$_2$N).

c) Hydrolysis of trityl protecting group i) Typical procedure. Place 20 mL aqueous hydrochloric acid (10% v/v) in a 100 mL round bottomed flask equipped with a magnetic stirrer bar and add 5.6 g (10.2 mmol) N,N-bis(triethyleneglycol methyl ether)trityl amine in 15 mL methanol dropwise. After addition is complete, stir for 30 man and filter the white precipitate. Remove the methanol on a rotary evaporator and wash the residue with 25 mL diethyl ether. Carefully neutralise the aqueous phase with saturated aqueous sodium hydrogen carbonate and evaporate the solvent to dryness. Extract the solid by trituration with 2×25 mL dichloromethane. Filter off the solid, dry over Na$_2$SO$_4$, and remove the solvent on rotary evaporator to leave a colourless liquid which does not need further purification.

N,N-bis(diethyleneoxymonomethyl)amine [HN((CH$_2$CH$_2$O)$_2$CH$_3$)$_2$], colourless liquid, yield 72%, IR (film) 3500, 3300, 1602 cm$^{-1}$, $^1H$ NMR (CDCl$_3$) δ3.5–3.7 (m, 12H, CH$_2$O), 3.4 (s, 6H, CH$_3$O), 2.8 (t, 4H, CH$_2$N), 2.25 (s, 1H, NH).

N,N-bis(triethyleneoxymonomethyl)amine [HN((CH$_2$CH$_2$O)$_3$CH$_3$)$_2$], colourless liquid, yield 75%, IR (film) 3500, 3300, 1602 cm$^{-1}$, $^1$H NMR (CDCl$_3$) δ 3.5–3.7 (m, 20H, CH$_2$O), 3.4 (s, 6FL CH$_3$O), 2.8 (t, 4H, CH$_2$N), 2.25 (s, 1H, NH).

N,N-bis(tetraethyleneoxymonomethyl)amine [HN((CH$_2$CH$_2$O)$_4$CH$_3$)2], colourless liquid, yield 62%, IR (film) 3500, 3300, 1602 cm$^{-1}$, $^1$H NMR (CDCl$_3$) δ3.5–3.7 (m, 28H, CH$_2$O), 3.4 (s, 6FI, CH$_3$O), 2.8 (t, 4H, CH$_2$N), 2.25 (s, H, NH).

IX Coupling of hydrophilic head group to oxygen binding fluorocarbon pockets i) Typical procedure. Add a mixture of one equivalent 4,4,4-tris(1H,1H-perfluoroheptyloxypropyl)butanoyl chloride and one equivalent triethylamine in 10 mL anhydrous THF to a three-neck round bottomed flask. Cool the mixture to 0° C. and add one equivalent N,N-bis(monomethytrioxethyl)amine dropwise. Stir at this temperature for 3 hr and allow the mixture to warm up to room temperature, and then stir for additional 4 hr. After reaction, acidify the mixture with cold aqueous HCl (5% v/v) and extract with 2×10 mL diethyl ether. Neutralise the aqueous phase with cold saturated aqueous sodium hydrogen carbonate and extract the product with 3×10 mL dichloromethane. Dry the organic phase over Na$_2$SO$_4$, evaporate the solvent under vacuum and purify the product by dry flash chromatography.

X Surface properties

Evaluation of the surface tension of some of these compounds reveal that they are surface active agents. Short fluoroalkyl chains (C$_n$F$_{2n+1}$ with n≦6) reduce the surface tension of their saturated aqueous solutions from 72 mN/m to about 45 mN/m at room temperature. Longer ones (n≦5) reduce similar solutions to about 20 mN/m which is within the range characteristic of fluorinated compounds. Coupling of the functionalised tris(hydroxymethyl)nitromethane derivatives with bis(trioxyethyleneglycol)amine as the hydrophilic head group gives water soluble molecules, presumably micellar solutions or microemulsions, at low concentrations of the surface-active molecules, and this can be associated with self-emulsification. Preliminary results show that large amounts of oxygen are dissolved by the system; detailed study is in progress.

I claim:

1. A compound for medical use in biological systems as an oxygen transport agent, consisting of:
   a carbon atom to which is attached:
   a) a non-hemolytic biocompatible hydrophilic head group and
   b) three lower alkylene groups, which are the same or different and to each of which is attached:
   a c3 to c16 carbon atom chain, saturated or unsaturated, straight chain or branched or cyclic or aromatic, in which more than half the H atoms are replaced by F atoms;
   wherein the said carbon atom chains are attached to the lower alkylene groups by linkages selected from the group consisting of ether, ester, amide, amine, sulfonamide and phosphoramide bond; and
   wherein the three lower alkylene groups and the carbon atom chains attached to them are constrained or predisposed to adopt a mutually cis relationship to each other to form or predispose to form a preorganized cage for oxygen incorporation.

2. A compound as claimed in claim 1, wherein each lower alkylene group is 1,3-propylene, and each carbon atom chain is —CH$_2$C$_3$F$_7$ and is attached to a lower alkylene group by an ether linkage.

3. A compound as claimed in claim 1, wherein the hydrophilic group comprises one or more alcohol, ether, carboxamide, sulfonamide, phosphoramide or N-oxide group in a linear, branched or cyclic configuration.

4. An aqueous emulsion containing 5–70% by volume of the compound defined in claim 1.

5. A compound for use in vivo as an oxygen transport agent, said compound having a structure selected from the group consisting of

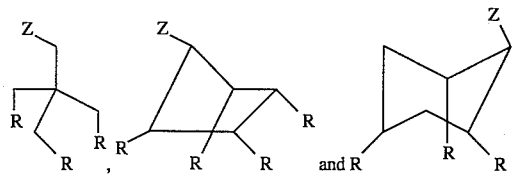

where Z is a non-hemolytic hydrophilic group and the groups R are the same or different and each is a lower alkylene group to which is attached:
a C$_3$ to C$_{16}$ carbon atom chain, saturated or unsaturated, straight chain or branched or cyclic or aromatic, in which more than half the H atoms are replaced by F atoms;
and wherein these groups R and the carbon atom chain attached to them are constrained or predisposed to adopt a mutually cis relationship to each other to form or predisposed to form a preorganized cage for oxygen incorporation.

6. A compound as claimed in claim 5, wherein the hydrophilic group comprises one or more alcohol, ether, carboxamide, sulphonamide, phosphoramide or N-oxide groups in a linear, or cyclic configuration.

7. A compound as claimed in claim 5, having the structure a) where Z is —CONH(CH$_2$)$_3$N(O) (CH$_3$)$_2$ or —CON(CH$_2$CH$_2$OCH$_3$)$_2$.

8. An aqueous emulsion containing 5–70% by volume of the compound defined in claim 5.

* * * * *